United States Patent
Roden et al.

(10) Patent No.: US 6,410,758 B2
(45) Date of Patent: *Jun. 25, 2002

(54) PREPARATION OF STEROL AND STANOL-ESTERS

(75) Inventors: Allan Roden, Noblesville, IN (US); James L. Williams, Reynoldsburg, OH (US); Ruey Bruce, Columbus, OH (US); Frank Detrano, Lancaster, OH (US); Marie H. Boyer, Fort Washington, PA (US)

(73) Assignee: McNeil-PPC, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/317,712

(22) Filed: May 24, 1999

(51) Int. Cl.⁷ .................................................. C07J 9/00
(52) U.S. Cl. ...................................................... 552/544
(58) Field of Search ........................................ 552/544

(56) References Cited

U.S. PATENT DOCUMENTS

| | | | | |
|---|---|---|---|---|
| 4,309,448 A | * | 1/1982 | Takaishi et al. | 424/365 |
| 4,822,875 A | * | 4/1989 | McCoy et al. | 536/119 |
| 5,061,503 A | * | 10/1991 | Kong-Chan et al. | 426/582 |
| 5,247,083 A | * | 9/1993 | Knox et al. | 544/153 |
| 5,437,714 A | * | 8/1995 | Cook et al. | 96/201 |
| 5,892,068 A | * | 4/1999 | Higgins | 552/554 |
| 5,958,913 A | | 9/1999 | Mietenen et al. | 514/182 |
| 6,063,957 A | * | 5/2000 | Koniger et al. | 560/218 |

FOREIGN PATENT DOCUMENTS

| | | | |
|---|---|---|---|
| EP | 0 897 970 A1 | 2/1999 | C11C/3/10 |
| EP | 0 911 385 A1 | 4/1999 | C11C/3/00 |
| WO | WO 95/00158 | 1/1995 | A61K/37/00 |
| WO | WO 99/30569 | 6/1999 | A23D/7/00 |
| WO | WO 99/39715 | 8/1999 | A61K/31/56 |
| WO | WO 99/43218 | 9/1999 | A23L/1/30 |
| WO | WO 99/59423 | 11/1999 | A23D/9/00 |

OTHER PUBLICATIONS

"Effect of Plant Sterol Esters on the Absorption of Dietary Cholesterol", The Procter & Gamble Company, Mattson, Volpenhein & erickson, J. Nutr. 107, pp. 1139–1146, (1977).

"Optimizing the Effect of Plant Sterols on cholesterol Absorption in Man", Mattson, Grundy, & Crouse, The American journal of Clinical Nutrition 35: Apr. 1982; pp. 697–700.

Mattson et al., "Effect of plant sterol esters on the absorption of dietary cholesterol." J. Nutr., vol. 107, pp. 113–1146, 1977.*

Merck Index, Ninth Edition, 1976.*

* cited by examiner

*Primary Examiner*—Barbara P. Badio

(57) ABSTRACT

The present invention provides a method for the direct esterification of stanols and sterols with fatty acids to form stanol/sterol-esters. The method provides a synthetic route that is amenable to large scale production of the esters in high yields. A preferred embodiment employs a food grade process free of organic solvents or mineral acids, does not produce or use non-food grade products and is substantially free of the use of a catalyst.

16 Claims, No Drawings

PREPARATION OF STEROL AND STANOL-ESTERS

FIELD OF THE INVENTION

This invention relates to the preparation of discrete sterol and stanol-esters through a highly efficient route free of catalyst producing a light colored product suitable for food use.

BACKGROUND OF THE INVENTION

It has been shown that the addition of plant sterols, such as. β-sitosterol, to diets will reduce serum cholesterol levels. The sterols reduce serum cholesterol through the disruption of intestinal absorption of dietary cholesterol by displacing it from bile acid micelli. More recently, β-sitosterol's saturated derivative, β-sitostanol, has been shown to be more effective in the reduction of intestinal cholesterol absorption. The sitostanol itself is virtually unabsorbed, so it does not contribute at all to in vivo serum sterol concentration upon consumption. Unfortunately, typical sterols and stanols are insoluble in the micelli phase of the alimentary canal and have only limited solubility in oils and/or fats or water. Hence, free sterols or stanols themselves are not optimum candidates for use in typical pharmaceutical or dietary dosage forms as cholesterol reducing agents.

U.S. Pat. No. 5,502,045 discloses the interesterification of stanols with a fatty acid ester from an edible oil to produce a waxy sterol-ester mixture with improved fat solubility characteristics. Specifically, this patent discloses the reaction of sitostanol interesterified with fatty acids from methyl esters of edible oil such as rapeseed oil specifically via a base catalyzed transesterification reaction. This is a process that is widely used in the food industry. From a pharmaceutical standpoint, however, interesterification processes such as this have some distinct disadvantages. Primarily, the composition profile of the sterol-ester products are difficult to control since the profile is dependent on the array of fatty acids present in the edible oil employed in the reaction. Also the need to use a large excess of methyl esters to drive the reaction to completion and the production of methanol, makes the purification to food grade material difficult.

In a different approach, German Patent 2035069 discloses the esterification of sterol-esters to fatty acids via a non-food grade process. In particular, thionyl chloride is employed as a reactant which when reacted forms HCl gases as a by-product. Such techniques are not suitable for the production of food grade materials, and they are undesirable in general for large scale reactions.

Japanese Patent 76-11113 discloses a catalyst free esterification of higher fatty acid esters of sterols or related vitamins. However this process employs a significant molar excess of fatty acid, a minimum of 25% up to 50%, which in turn requires the use of an alkali refining process to recover the ester product. The stoichiometric excess fatty acid and the isolation techniques result in a product that is discolored.

From a pharmaceutical standpoint, there is an unmet need for a method for the synthesis of discrete stanol/sterol-esters via a bulk food grade process. Discrete compounds are more desirable than mixtures for three main reasons: 1) the composition and performance specifications can be controlled better; 2) structure/activity studies are more feasible; and 3) the physicochemical and chemical properties can be controlled. These advantages of discrete stanol/sterol-esters will be elaborated on later.

SUMMARY OF THE INVENTION

The present invention comprises a method for the direct esterification of stanols or sterols with fatty acids to form discrete stanol/sterol-esters that are light in color, free of off flavors and odors. The method provides a one step synthetic route that is amenable to large scale production of the sterol-esters/stanol-esters and other related cholesterol reducing compound esters in high yield and purity by a food grade process that in a preferred embodiment is free of organic solvents, mineral acids and avoids the production of objectionable by products. The method ultimately provides a convenient process that enables one to rationally design discrete stanol/sterol-esters with various physical and biological properties.

DETAILED DESCRIPTION OF THE INVENTION

The present invention provides the direct esterification of stanols and sterols through the reaction of the stanol/sterol and a fatty acid substantially free of the use of a catalyst. As used in the present invention, substantially free of catalyst is understood to means less than about 0.15% by weight of reaction, and in a preferred embodiment the reaction takes place in the absence of a catalyst. Suitable catalyst include toluene sulfonic acid, methane sulfonic acid, sodium hydrogen phosphate, sodium bisulfite and the like. These catalysts are disclosed in U.S. Pat. No. 5,892,068 hereby incorporated by reference.

β-sitostanol, the most preferred starting material, is commercially produced from β-sitosterol by a hydrogenation reaction and is commercially available, from various sources including Henkel Corporation.

In the present invention the sterol and stanol-esters have the general formula depicted as FIG. I:

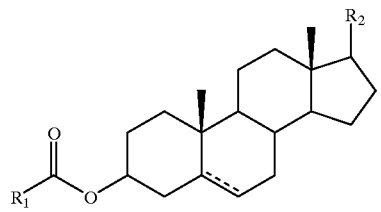

FIG. I wherein $R_1$ is understood to include aliphatic straight or branched carbon chains having a length of from $C_4$-$C_{24}$, preferably from $C_6$-$C_{20}$ and most preferably $C_{12}$-$C_{18}$, and $R_2$ is understood to include aliphatic straight or branched carbon chains ranging $C_3$-$C_{15}$, preferably $C_6$-$C_{12}$, and most preferably, $C_8$-$C_{10}$. More preferably, $R_2$ is selected from the group ($C_1$-$C_{12}$) alkyl, ($C_1$-$C_8$) alkoxy, ($C_2$-$C_8$) alkenyl, ($C_2$-$C_8$) alkynyl, ($C_3$-$C_8$) cycloalkyl, halo ($C_2$-$C_8$) alkenyl, halo ($C_2$-$C_8$) alkynyl) where halo is understood to include chloro, fluoro, bromo, iodo and the like. Alkyl includes both straight and branched chain groups of carbon atoms. Typical alkyl groups include methyl, ethyl, n-propyl, isopropyl, n-butyl, sec-butyl, isobutyl, t-butyl, n-pentyl, neopentyl, isopentyl, hexyl, heptyl and the like. The alkyl groups may be halogenated with one, two three or more halogen atoms. $R_2$ may also be a saturated branched alkane chain.

The terms alkenyl and alkynyl included branded and straight chain hydrocarbons having at least one unsaturated bond.

The acids, which include the associated salts, reacted in the present invention contain from 4 to 24 carbon atoms. The acids include saturated acids, but are preferably unsaturated fatty acids, including polyunsaturated fatty acids. The saturated fatty acids reacted in the present invention are of the formulae $CH_3$—$(CH_2)_n$—$CO_2H$ wherein n is an integer of from about 2 to about 22, and more preferably n is from about 12 to about 20. The term fatty acid is well known and understood to those with skill in the art, see for example, *Hawley's Condensed Chemical Dictionary*, Eleventh edition. The fatty acids include both saturated acids, such as stearic, butyric, lauric, palmitic and the like. Unsaturated fatty acids can also be used in the present invention and include oleic, linoleic, linolenic, docosohexanoic acid, conjugated linoleic acid (9,11-octadecadienoic acid, 10, 12-octadecadienoic acid) mixtures of the acids, and the like.

In a more preferred embodiment, the sterol and stanol-esters have the general formula depicted as FIG. II:

FIG. II

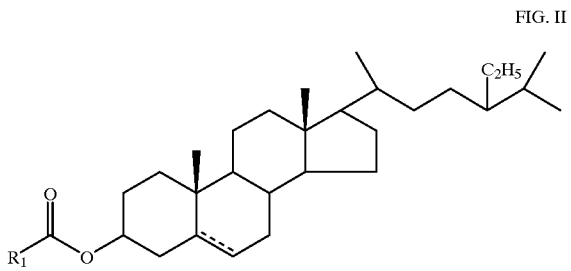

wherein $R_1$ is understood to have the same meaning as set forth above. Unsaturation at $C_5$ as shown gives the corresponding sterol-ester.

The present invention can be employed to esterify a wide range of cholesterol lowering or cholesterol limiting substances. These substances, including stanols or sterols, all contain a hydroxy functional hydroxy group which is suitable for esterification by the process described herein. Stanols that are capable of being esterified in the present invention include, but are not limited to β-sitostanol (depicted in FIG. III below) as well as other related compounds including cholestanol, ergostanol, brassicastanol, avenastanol, alpha-amyrin, cylartenol, lupenol and the like.

FIG. III

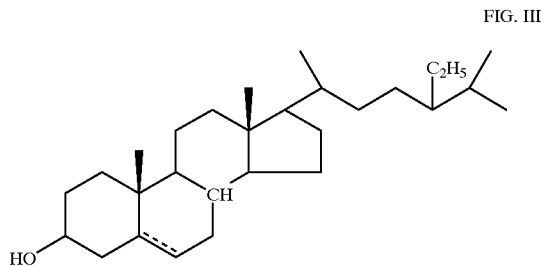

For example, this process is also amenable to sterols such as β-sitosterol (unsaturated at $C_5$, as shown in FIG. II above) as well as the corresponding sterols to above named stanols.

The molar ratios of the starting materials for the esterification reaction, notably the stanol/sterol and the fatty acid, are provided with a slight molar excess of the fatty acid, preferably less than about 10% molar excess. In a highly preferred embodiment, the fatty acid is present in a 5-10% excess so as to react all of the stanol/sterol or other cholesterol reducing material. Any excess unreacted fatty acid is easily removed in the product workup. The process is limited to a slight molar excess of fatty acid so that excessive amounts do not need to be removed. The removal of excess fatty acid has a deleterious effect on product color and quantity.

The reactants are provided to a suitable vessel and heated to a temperature of from about 110 to about 130° C., preferably under a vacuum, to melt the reactants and to remove any volatile material present. Then the contents of the vessel are heated to a temperature of from about 165 to about 255° C., preferably from about 190 to about 250° C., more preferably from about 190 to about 230° C. The reaction is preferably conducted under vacuum conditions to facilitate the removal of water which drives the reaction to completion. When the level of free fatty acid content falls to less than about 10 weight percent, preferably less than about 6 weight percent, the temperature of the reaction is increased to about 230 to about 240° C. At this time the level of foaming in the vessel has also dropped which is another indication that it is appropriate to raise the temperature of the vessel.

After the desired free fatty acid level is achieved it is preferable to initiate a steam sparge. The steam sparge is an effective technique to remove excess or unreacted fatty acids from the reactor. The reaction is complete when the fatty acid content falls below 1 weight percent, preferably less than about 0.5 weight percent and more preferably less than about 0.2 weight percent.

One of the most effective aspects of the present invention is that the reaction is preferably performed neat, wherein no solvents are added to the reaction mixture, because the acid, particularly fatty acids, acts as both a reactant and solvent. In addition, no toxic solvents or by products are produced during the reaction, such that water is the only reaction by-product be water which is easily removed.

It is particularly appropriate to run the neat reactions under vacuum in order to remove water from the reaction mixture thereby driving the reaction to completion and increasing the yield of the desired ester. When the reaction is conducted neat and a steam sparge is employed to remove unreacted fatty acid, the reaction product is easily and cost effectively recovered from the reaction vessel.

Reaction times of greater than 8 hours are common but not necessarily required. One advantage of the present invention is the high yield of the ester product provided by the process. The present process provides yields of greater than 90% and preferably greater than 95% based on the total charge to the reactor. Yields greater than 98 and preferably greater than 99 percent are achieved based on the stanol/sterol charge to the reactor.

A further advantage is the fact that no water washing is required for the removal of the catalyst or by-products of the reaction. The present invention results in faster processing of the material and lower losses, reducing the cost of the process. Furthermore, this reaction is conducted in one vessel reducing capital equipment costs and eliminating expensive material handling and transfers between vessels and processes.

A further advantage of the present invention is the addition of a suitable amount of a color deactivating agent. Typically the amount of the color deactivating agent is from about 0.05% to about 1% weight percent based upon the reaction total weight; preferably from about 0.2 to about 0.5%; and most preferably from about 0.35 to about 0.45 weight percent Suitable color deactivating agents include carbon, charcoal and carbon black; edible oil, bleaching earth, or a silica bleaching such as Trisil from Grace Chemical, of which charcoal is preferred. The color deactivating agent prevents the reaction product from becoming discolored, i.e., not white and the color deactivating agent is preferably incorporated with either the stanol/sterol and acid in the reaction vessel.

The resulting product of the present invention is white, free from off flavors and other volatile material with a bland flavor. The resulting stanol ester/sterol-ester product has a Gardner color value of less than 5, preferably less than about 4 and most preferably less than about 3 on the Gardner color scale. The Gardner color scale is known to those in the art. The product of the reaction are formed into a block and the color block is compared to samples of a predetermined color. Earlier processes provided product with higher color values. For example, the stanol esters produced in accordance with U.S. Pat. No. 5,892,068, had a Gardner color value of from about 7 to about 10. Using the process described in Japanese Patent 76-11113, the products had Gardner color values of from about 10 to about 12.

The reaction product can be dissolved in oil and added to any food product that contains an oil component. Another advantage of the present invention is the elimination of the need for washing of the product to deactivate or remove any catalyst that may be contained in the resulting product. Another advantage of the present invention is the production of a lower color product than other stanol or sterol ester products produced with a catalyst.

The present invention provides several advantages over previous disclosed processes. The present invention provides a method to synthesize substantially discrete stanol-esters rather than mixtures of stanol-esters. As used herein, substantially discrete is understood to mean that the reaction product, the desired ester is provided in a very high proportion of the reaction product. Typically the desired ester is provided in the reaction product in at least 90 percent by weight, more preferably in an amount at least about 98 percent and if the reaction is allowed to run to completion to at least 99 percent by weight. The present invention is capable of providing essentially a single stanol/sterol-ester, with less than 0.2 weight percent of other ester products. The previously disclosed interesterification processes provide a mixture of the stanol-ester products. For example, the previously disclosed processes provide mixtures of stanol-esters, often with broad ranges of the stanol-esters present (for example, a mixture of 4 esters in ratios of 30, 30, 20, 20 percent by weight). Also in comparison, the previously disclosed direct esterification processes use hazardous, deleterious reagents produce by products which must be completely removed.

This production of discrete stanol/sterol-esters has several important advantages over the stanol/sterol-ester mixtures produced by other processes. Firstly, tighter performance specifications (i.e., melting point, specific gravity structural species purity) are possible for discrete compounds. This is because the properties of discrete compounds can be controlled with more precision than for mixtures. Hence, proper performance characteristics and quality of discrete esters are more easily assured as compared to a mixture of ester products.

Furthermore, because the present invention provides the synthesis of discrete stanol/sterol-esters, structure/activity relationships over a range of fatty acid chain lengths can be ascertained. The determination of structure/activity relationships, which are fundamental to rational drug development, are only feasible when screening discrete compounds.

Finally, the gross physical and physiologic properties of the sterol/stanol-ester can be controlled since those properties are dependent upon which fatty acid is employed. For example, esterification to unsaturated fatty acids (i.e., oleic acid) can lead to low melting solids or even liquid products, whereas saturated fatty acid analogs (i.e., stearic acid) tend to lead to higher melting free flowing solids. This ability to so extensively manipulate the physical properties of a high melting steroid is quite unexpected.

The present invention allows the selection of the ester to match the physical properties which are desired. The solid free flowing material is desirable for the manufacture of compressed tablets, or the incorporation of the stanol-ester into baking products. These oil-like stanol/sterol-esters are advantageously employed in the manufacture of tablets or soft gel dosage forms or incorporated into suitable foods such as salad dressing, margarine or yogurt.

The following examples are provided to further illustrate the claimed invention, but not limit the invention to the examples provided below.

EXAMPLE 1

Reaction with 10% excess of fatty acids 1250.1 grams of stanols from Raisio were added to a three-neck flask equipped with a mixer. To this, 928.1 grams of Canola oil fatty acids (Emery 790 from Henkel) was added along with 10.95 grams of carbon black. The mixture was heated under vacuum to 134° C. until visible bubbling stop showing complete removal of air and volatile materials. Heating was then continued to 245° C. where the product was under vacuum of 5 mm of mercury for 11 hours after which the acid value was reduced to 3.23 milligrams of KOH/gram of sample. The resulting product was then deodorized by sparging steam through the material at 245° C. and 5 mm of mercury pressure for 9 hours.

The resulting product was stanol ester with more the 95% of the stanol converted to the ester form. The product was light yellow, with a slight burnt flavor, with a melt point of 33.8° C. and an acid value of 0.22.

EXAMPLE 2

Reaction with 5% excess fatty acids using linoleic acid.

1130 grams of stanols from Raisio, 795.4 grams of linoleic acid (Emersol 315 from Henkel) and 9.68 grams of carbon were added to the flash and deaerated and heated as above. After 7 hours at 245° C. the acid value and 5 mm of Hg the acid value was 8.35. The material was deodorized as above to an acid value of 0.23. This product was a light yellow liquid that partially crystallized over night to a thick paste with a melting point of 17.5° C., the flavor was acceptable. When compared to Example 1, this example demonstrates the ability to change the melting point by modifying the fatty acids used in the reaction.

EXAMPLE 3

Reaction with 5% molar excess of fatty acid and no carbon black.

909.1 grams of Stanols from Raisio and 648.6 grams of oleic acid (Pamoyln 100 from Hercules Chemicals) were mixed and heated together 167° C. with out vacuum. During this time, a slow reaction was observed indicated by a slow accumulation of water in the condenser. When the vacuum was started and the pressure was reduced to 5 mm of Hg the reaction rate increased. The temperature was increased to 211° C. and held at this temperature for 5 hours. The acid value was reduced to 16.79 indicating the reaction was proceeding. The product color was light brown with a Gardener color of greater than 7. When compared to the example 4 this shows the benefit of using carbon black in the reaction.

EXAMPLE 4

Canola fatty acids at 5% molar excess

Using the same procedures as set forth in Example 2 above, with carbon black canola oil fatty acid stanol esters were produced. The reaction time required was 8 hours resulted in a acid value of 8.64. This product had a melting point of less than 36° C. a clean flavor and a color of 3 on a Gardner scale.

We claim:

1. A method for producing stanol/sterol-esters comprising providing a stanol/sterol of the formula

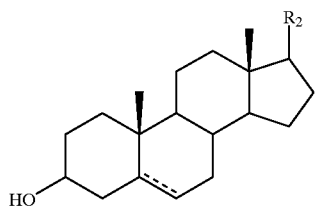

providing less than about 10% molar excess of a $C_4$-$C_{24}$ acid relative to the sterol/stanol, admixing and heating said stanol/sterol and acid at a temperature of from about 150 to about 260° C., free of catalyst and added solvents, resulting in the production of the substantially discrete corresponding food grade stanol/sterol ester of the formula,

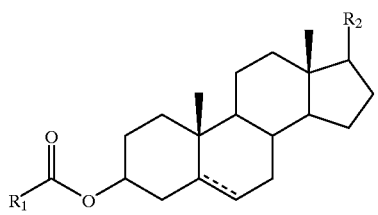

wherein $R_1$ is a carbon chain having a length of from about from about $C_4$ to about $C_{24}$; and $R_2$ is a carbon chain having a length of from about $C_3$ to about $C_{15}$.

2. The method of claim 1 wherein the a color deactivator is employed.

3. The method of claim 2 wherein the color deactivator is charcoal.

4. The method of claim 1 wherein the acid is fatty acid of the formula $CH_3$—$(CH_2)_n$—$CO_2H$ where n has a value of from about from 2 to 22.

5. The method of claim 1 wherein the stanol/sterol and acid is admixed and heated under vacuum.

6. A method for producing stanol/sterol esters comprising providing a stanol/sterol of the formula

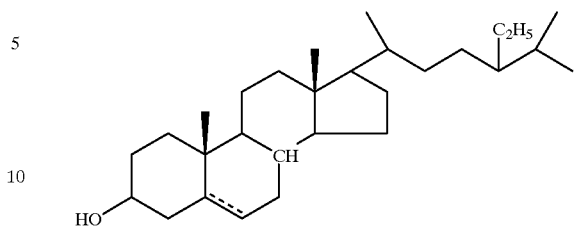

providing less than about a 10% molar excess of a fatty acid of the formula $CH_3$—$(CH_2)_n$—$CO_2H$ relative to the sterol/stanol wherein n is an integer of from 4 to 22;
admixing and heating said stanol/sterol and fatty acid, free of catalyst and added solvents, resulting in the production of the corresponding food grade stanol/sterol-ester.

7. The method of claim 6 wherein the heating is conducted at a temperature of from about 150 to about 260 C.

8. The method of claim 6 wherein the a color deactivator is employed.

9. The method of claim 8 wherein the color deactivator is charcoal.

10. The method of claim 6 wherein n of the fatty acid has a value of from about from $C_{12}$ to $C_{20}$.

11. The method of claim 6 wherein the stanol/sterol and fatty acid is heated at a temperature of from 190 about to about 250° C.

12. The method of claim 6 wherein the stanol/sterol and fatty acid is admixed and heated under a vacuum.

13. A method for providing an ester comprising
providing a compound selected from the group consisting of β-sitostanol, β-sitsterol, cholestanol, ergostanol, brassicastanol, avenastanol, alpha-amyrin, cylartenol, and lupenol;
providing a less than about 10% molar excess of a fatty acid of the formula $CH_3$—$(CH_2)_n$—$CO_2H$ wherein n is an integer of from 2 to 22;
admixing and heating said compound and fatty acid free of any catalyst and added solvent at a temperature of from about 160 to about 255° C. resulting in the production of the corresponding food-grade esterified compound.

14. The method of claim 13 wherein the esterification reaction is conducted in the presence of an effective amount of a color deactivating agent.

15. The method of claim 14 wherein the color deactivating agent is charcoal.

16. The method of claim 15 wherein the excess fatty acid is removed by steam sparging.

* * * * *